United States Patent [19]

Tanner et al.

[11] Patent Number: 5,028,422
[45] Date of Patent: Jul. 2, 1991

[54] TREATMENT OF BASAL CELL CARCINOMA INTRALESIONALLY WITH RECOMBINANT HUMAN ALPHA INTERFERON

[75] Inventors: Daniel J. Tanner, Brooklyn; Edwin A. Peets, New York; Kenneth A. Smiles, Windsor, all of N.J.

[73] Assignee: Schering Corporation, Kenilworth, N.J.

[21] Appl. No.: 337,586

[22] Filed: Apr. 13, 1989

Related U.S. Application Data

[63] Continuation-in-part of Ser. No. 866,644, May 27, 1986, abandoned.

[51] Int. Cl.$^5$ ............................................. A61K 37/66
[52] U.S. Cl. ................................... 424/85.4; 424/85.7
[58] Field of Search ............................. 424/85.7, 85.4

[56] References Cited

U.S. PATENT DOCUMENTS

| | | | |
|---|---|---|---|
| 4,289,690 | 9/1981 | Pestka et al. | 260/112 R |
| 4,503,035 | 3/1985 | Pestka et al. | 435/68 |
| 4,530,901 | 7/1985 | Weissman | 435/811 |
| 4,959,210 | 9/1990 | Smiles et al. | 424/85.4 |

FOREIGN PATENT DOCUMENTS

| | | |
|---|---|---|
| 0077063 | 4/1983 | European Pat. Off. . |
| 0770063 | 4/1983 | European Pat. Off. . |
| 0032134 | 4/1984 | European Pat. Off. . |
| 233629 | 8/1987 | European Pat. Off. . |
| 0248583 | 12/1987 | European Pat. Off. . |
| 0281299 | 9/1988 | European Pat. Off. . |
| 281299 | 9/1988 | European Pat. Off. . |
| 0305551 | 3/1989 | European Pat. Off. . |
| 8302458 | 2/1983 | World Int. Prop. O. . |
| 8302457 | 7/1983 | World Int. Prop. O. . |
| 8302460 | 7/1983 | World Int. Orop. O. . |

OTHER PUBLICATIONS

Ikeda, Japan Journal of Cancer Chemotherapy, 12(4), 936-942 (1985).
Ikic, D., Interferon and Cancer (Editor, Sikora K.), 169-181, Plenum Press (1983).
Barenbein et al., Vestn. Dermatology, Venerol No. (4): 31-33 (1985).
Ikic et al., The Lancet, May 9, 1981, pp. 1025-1027.
Langer et al., J. Invest. Dermatology 63, 1285-1365 (1984).
Staehelin et al., Methods in Enzynology 78 Part A. 505,511 (1981) Academic Press, N.J.
Rubenstein, Biochem. Biophys. Acta. 695, 5-16 (1982).
Nagata et al., Nature 284, 316-320 (1980).
Rook et al., Textbook of Dermatology, Fourth Edition, vol. 3 (Blackwell Scientific Publications), p. 2431-2437.
The Merck Index, Eleventh Edition (Merk & Co., Inc., Rahway, N.J.), p. 4895 (1989).
Genetic Tech. News, 6, No. 10, 1986, p. 5 (Greenway et al.).
J. Am. Acad. Dermat., 15 No. 3, Sept. 1986, pp. 437-443 (Greenway et al.)
Smiles et al. The Biology of the Interferon System, pp. 493-501.
Morita et al., Acta Dermatol-Kyoto 81(2), pp. 241-246, 1986.
Eron et al., The New England Journal of Medicine, vol. 315, No. 17, pp. 1059-1064 (1986).

Primary Examiner—F. T. Moezie
Assistant Examiner—Andrew G. Rozycki
Attorney, Agent, or Firm—Henry C. Jeanette; Eric S. Dicker; Gerald S. Rosen

[57] ABSTRACT

This invention relates to a method of treating basal cell carcinoma with purified human recombinant DNA interferon alpha-2, preferably purified human recombinant DNA interferon alpha-2b by administering intralesionally (by injection) to a patient in need of such treatment, a sufficient amount of the purified human recombinant DNA alpha interferon, preferably recombinant DNA interferon alpha-2b, to be effective as an antitumor agent.

4 Claims, No Drawings

TREATMENT OF BASAL CELL CARCINOMA INTRALESIONALLY WITH RECOMBINANT HUMAN ALPHA INTERFERON

RELATED APPLICATIONS

This is a continuation-in-part of U.S. patent application Ser. No. 866,644, filed May 27, 1986, now abandoned, the priority of which is claimed.

BACKGROUND

This invention relates to a method of treating basal cell carcinoma with recombinant human alpha interferon by administering the interferon directly into the carcinoma lesion, i.e. intralesionally.

Basal cell carcinomas are the most common cutaneous neoplasms found in humans. The majority of the 500,000 new cases of nonmelanoma skin cancers each year are basal cell carcinomas.

Basal cell carcinomas exist in a variety of clinical and histological forms such as nodular-ulcerative, superficial, pigmented, morphealike, fibroepithelioma and nevoid syndrome. Present treatment methods include various surgical techniques such as electrodesiccation and curettage, excision, cryosurgery and irradiation. Cure rates for the surgical techniques are generally stated to be about 95%. Despite the high cure rates effected by surgical techniques, non-surgical methods of therapy are generally thought to be more desirable.

Various efforts have been made to treat cancers by injecting interferon directly into the lesion. For example, Ikeda, Gan to Kagaku Ryoho, 12(4), 936-942 (1985) used recombinant interferon A to treat various malignant skin tumors and achieved low cure rates. None of the tumors treated were stated to be basal cell carcinomas. Sikora, K. (Editor), *Interferon and Cancer*, Ikic, D., Intralesional Therapy, 169-181, Plenum, N.Y. (1983) used unpurified human leukocyte interferon to treat basal cell carcinoma patients intralesionally. Ikic did not use a purified interferon material, but used a material containing a mixture of leukocyte interferon components and non-interferon impurities.

Barenbein, et al., Vestn. Dermatol. Venerol. No. (4): 31-33 (1985) used a "new Soviet interferon preparation, human leukocyte interferon for injection II" to treat skin basal cell carcinoma. It is not clear from the article if the "new" interferon is a recombinant human alpha interferon. The duration of the course of treatment varied from 10 to 20 days with a maximum dose of 100,000 International Units. The patients were injected twice daily for ten days, in a dose of 2,500–5,000 International Units, until a total dose of 50,000–100,000 IU was reached. This dosage is different than required to achieve the results of the present invention. Ikic et al., The Lancet, May 9, 1981, pp. 1025-1027, discloses local administration of crude leukocyte interferon to cancer patients, including those with basal cell carcinoma. Langer et al., Journal of Investigative Dermatology, 83, 128s–136s (1984) discloses purification, bacterial expression and biological activities of human interferons. Langer et al. state "Subsequent work has demonstrated that there are at least 10 highly related human alpha interferons (IFN-$\alpha$) each with characteristic chemical and biological properties and each encoded by a different gene". In a discussion of leukocyte interferons, Langer et al. on page 130s stated:

"The purification of naturally induced human leukocyte interferons conclusively established several concepts; (1) Multiple leukocyte interferon species can be induced simultaneously in cultured human cells. This immediately suggested the existence of multiple genes corresponding to each of these structurally distinct species. (2) These interferons are closely related, having similar, but not identical molecular weights, amino acid content, and cryptic maps. (3) Although all the species were active on both human and bovine cells, the relative specific activities, particularly on human cells, differed considerably. (4) No carbohydrate was detected on five of the purified species examined. This contradicted the previously accepted notion that all interferons were glycoproteins."

and noted that the leukocyte interferons had different activities: "It was found that all the species exhibited antiproliferative activity on these cells [human lymphoblastoid Daudi cell line], although their potencies differed. This supported the notion that the chemical differences of the leukocyte interferon species are reflected in functional differences."

Langer et al. further observed that:

"If the various effects of interferon—antiviral, antiproliferative, natural killer cell activation, etc.—were all mediated through the same biochemical pathway, then it might be expected that the potency of a species in one assay would correlate with its potency in another assay. However, this was not observed."

There is no discussion in Langer et al. regarding treatment of basal cell carcinoma. Staehelin et al., Methods in Enzymology, Pestka ed., 78, 505,511(1981), published prior to Langer et al. supra, discusses a homogeneous human leukocyte prepared from bacterial fermentations. The authors state: "The recombinant IFLrA exhibits antiviral activity and antiproliferative activity comparable to crude and purified natural leukocyte interferons." The identity of the species of interferon is not apparent, so it cannot be ascertained which of the numerous leukocyte interferon species is being discussed. There is no discussion of treatment of basal cell carcinoma.

Weissman, U.S. Pat. No. 4,530,901 discloses a means to make leukocyte type interferons with recombinant DNA molecules.

Interferons are a family of proteins which exhibit antiviral activity against certain viruses and anticancer activity against certain cancers. There are three types of interferons; alpha or leukocyte interferon, beta or fibroblast interferon and gamma or immune interferon. Human alpha interferon is a naturally occurring mixture of at least eleven components including those designated alpha-1 interferon and alpha-2 interferon. Human alpha interferon exhibiting biological properties similar to those of naturally occurring human leukocyte interferon can be made by recombinant methods.

A number of alpha interferon species or components are known and are usually designated by a numeral after the Greek letter alpha, and all are contemplated for use in this invention. Thus, the species designated human alpha-1 interferon and human alpha-2 interferon (sometimes called human alpha-2 interferon which includes human alpha-2$a$ and human alpha-2$b$ interferon; USAN: Interferon Alfa-2 including Interferon Alfa-2$a$ and Interferon Alfa-2b) are contemplated, with human alpha-2 interferon preferred and Interferon Alfa-2b most preferred. Interferon alfa-2 can be produced in bacteria using recombinant techniques as disclosed in Rubenstein, Biochem. Biophys. Acta, 695, 5–6 (1982). In addition, interferon alfa-2 may be prepared by recombinant-DNA methods disclosed by Nagata et al., Nature, 284, 316–320 (1980), European Patent 32,134 and U.S. Pat. No. 4,289,690. Various alpha-2-interferon species are disclosed in U.S. Pat. No. 4,503,035. Preferred for use in this invention is purified human recombinant DNA interferon alfa-2b.

SUMMARY OF THE INVENTION

This invention relates to a method of treating basal cell carcinoma with purified human recombinant DNA interferon alpha-2preferably purified human recombinant DNA interferon alpha-2b by administering intralesionally (by injection) to a patient in need of such treatment, a sufficient amount of the purified human recombinant DNA alpha interferon, preferably purified recombinant DNA interferon alpha-2b, to be effective as an antitumor agent.

DETAILED DESCRIPTION

As used herein "alpha interferon" means purified human recombinant DNA interferon alpha-2 which includes purified human recombinant DNA interferon alpha-2a and purified human recombinant DNA interferon alpha-2b. In most instances this invention will be described in the following discussion using the preferred interferon as purified "human recombinant DNA interferon alpha-2b" or "interferon alpha-2b".

For intralesional administration, liquid injectable pharmaceutically acceptable compositions are used. Such compositions can, for example, be prepared by diluting freeze dried purified human recombinant DNA interferon alpha-2b with sterile water with or without preservatives although one with preservatives is preferred, to produce an isotonic solution containing the appropriate concentration of the interferon. Other injectable compositions using saline, aqueous dextrose, glycerol, ethanol and the like, to thereby form a solution or suspension for injection can also be used. If desired, minor amounts of nontoxic auxiliary substances such as wetting or emulsifying agents, preservatives, pH buffering agents and the like, for example, sodium acetate or sorbitan monolaurate, can be incorporated into the compositions. Actual methods of preparing such dosage forms are known, or will be apparent, to those skilled in this art; see for example, *Remington's Pharmaceutical Sciences*, Mack Publishing Company, Easton, Pa., 15th Edition, 1975. The amount of interferon alpha-2b administered is critical only to the extent that it is effective for the therapeutic purpose. The quantity in the composition or formulation administered will, in any event, be an amount effective to achieve an anti-basal cell carcinoma effect in the subject being treated.

The amount of purified human recombinant DNA interferon alpha-2b in a 0.15 ml. injectable dosage is about $1.5 \times 10^6$ I.U. (International Units), however, if a range of dosages is required, such dosages can be made, e.g., vials can be made with $5 \times 10^6$ to $2.25 \times 10^7$ I.U.

Clinical tests to determine the effect of the purified interferon alpha-2b on basal cell carcinoma were conducted. In one test, interferon alpha-2b was administered in doses of $1.5 \times 10^6$ I.U. three days a week for three weeks, i.e. $13.5 \times 10^6$ I.U. total. In another test the purified interferon alpha-2b was administered with six injections of $2.25 \times 10^6$ I.U. over two weeks, i.e. $13.5 \times 10^6$ I.U. total. In another test, patients with basal cell carcinoma lesions of from 3–10 cm² received about $0.5 \times 10^6$ I.U./cm² of initial lesion area of purified interferon alpha-2b three times a week every other day for three weeks (9 doses), i.e. a total of from $13.5 \times 10^6$ I.U. to $45 \times 10^6$ I.U. per patient depending on the size of the lesion. Patients with basal cell carcinoma lesions of from 2–3 cm² may receive $1.5 \times 10^6$ I.U. of purified interferon alpha-2b three times a week for three weeks, i.e. a total of $13.5 \times 10^6$ I.U. units.

Although these doses and the regimen described were beneficial, it is contemplated that they be considered only guidelines and that the attending clinician will determine, in his or her judgment, an appropriate dosage and regimen, using the patient's age and condition as well as the severity of the basal cell carcinoma.

The following illustrates the effects of treating patients having basal cell carcinoma with intralesionally administered interferon alpha-2b.

CLINICAL STUDY I

PATIENTS AND METHODS

Patients

Eight patients, six males and two females, each with one biopsy proven primary basal cell carcinoma of the nodular (3 patients) or superficial (5 patients) type were included in the study. The lesions, which varied in size from $7 \times 6$ mm to $14 \times 12$ mm, were located on the back (5), shoulder (1), arm (1) and neck (1). The diagnosis of nodular or superficial basal cell carcinoma was confirmed by incisional biopsy at least one week prior to the initiation of treatment.

Each patient was in good health and elected to be treated with interferon alpha-2b rather than undergo other ablative or surgical procedures.

Laboratory Test

Laboratory tests, hematology, serum chemistries and urinalysis were performed prior to, during and following treatment.

Treatment

Treatments were conducted with freeze-dried purified human recombinant DNA alpha-2b interferon which was in vials. The interferon the vials was diluted with sterile, preservative-free water to produce an isotonic solution containing sufficient interferon concentration so that 0.15 ml of solution contained $1.5 \times 10^6$ International Units (IU). Each lesion was injected with 0.15 ml of interferon alpha-2b with a 30-gauge needle on a tuberculin syringe. The needle was inserted tangentially into the lesion with care being taken to inject the entire amount intralesionally. The procedure was repeated for a total of three injections per week for three weeks. Thus, each lesion was injected with a total of $13.5 \times 10^6$ I.U.

Patients were evaluated during the treatment for clinical response and side effects. Evaluations were continued at one, four and eight weeks after completion of treatment. Systemic side effects (i.e. flu-like symptoms) were treated and controlled with oral acetaminophen.

Response Criteria

Excisional biopsy was performed on the lesional test site of each of the eight patients eight weeks following completion of the treatment with interferon alpha-2b. Multiple serial sections were examined histopathologically after staining with hematoxylin and eosin. Clinical responses were measured during treatment and follow-up visits through evaluation of changes in lesion size, erythema and, in the case of nodular lesions, percentage of flattening.

The following Table I shows the results of treatment of basal cell carcinoma with purified recombinant DNA human interferon alpha-2b.

TABLE I

Results of Treating Basal Cell Carcinoma with Interferon Alpha-2b.

| Case | Age | Sex | Type of Basal Cell Carcinoma | Pre Treatment Lesion Size (mm) | Post Treatment Lesion Size (mm) | % Lesion Flattening (nodular lesions only) | Follow-up Excisional Biopsy |
|---|---|---|---|---|---|---|---|
| 1 | 59 | M | superficial | 8 × 8 | 6 × 3 | — | No tumor noted |
| 3 | 63 | M | superficial | 8 × 5 | 0 | — | No tumor noted |
| 5 | 50 | F | superficial | 14 × 12 | 3 × 2 | — | No tumor noted |
| 7 | 51 | M | superficial | 11 × 8 | 6 × 4 | — | No tumor noted |
| 8 | 58 | M | superficial | 12 × 10 | 6 × 4 | — | No tumor noted |
| 2 | 52 | M | nodular | 7 × 6 | 5 × 4 | 100 | No tumor noted |
| 4 | 50 | F | nodular | 9 × 8 | 6 × 3 | 100 | No tumor noted |
| 6 | 48 | M | nodular | 11 × 6 | 6 × 4 | 100 | No tumor noted |

As is apparent from the data in Table I, all the basal cell carcinomas were eliminated. This was confirmed by histopathologic study.

The sites where the basal cell carcinomas had been treated demonstrated ectasia of vessels in the papillary dermis, perivascular lymphocytic and histiocytic accumulations, and in some cases lymphocyte exocytosis, civatte body formation and incontinence of pigment. No "tumor" stroma, necrotic basal cell carcinoma, polymorphonuclear neutrophil leukocytes (PMN), transformed lymphocytes or eosinophils were found.

SIDE EFFECTS

No life threatening or serious treatment related side effects were found as shown in the following Table II.

TABLE II

Side Effects when Treating Basal Cell Carcinoma with Interferon alpha-2b.

| Patient # | 1 | 2 | 3 | 4 | 5 | 6 | 7 | 8 | Total |
|---|---|---|---|---|---|---|---|---|---|
| Fever (p first dose) | + | + | + | + | + |   |   | + | 6 |
| Fever (p other doses) |   |   | + | + |   | + |   |   | 3 |
| Malaise | + |   |   |   | + | + | + | + | 5 |
| Itching (at site) |   | + |   | + |   |   | + |   | 3 |
| Lightheadedness |   |   | + |   |   |   |   |   | 1 |
| Pain (at site) |   |   |   | + |   |   |   |   | 1 |
| Muscle aches |   |   |   | + |   |   | + |   | 2 |
| Joint aches |   |   |   | + |   | + |   |   | 2 |
| Depressive mood |   |   |   | + |   |   |   |   | 1 |
| Headache |   |   |   |   |   | + | + |   | 2 |
| Abdominal discomfort |   |   |   |   | + |   |   |   | 1 |
| Chills |   |   |   |   |   |   | + |   | 1 |

All of the above were mild or moderate, except some of the malaise symptoms were severe.

As the data in Table II indicate fever was the most common side effect followed by malaise. All side effects were transient and reversible, and all patients were able to complete the treatment regimen.

White blood cell counts were diminished in three patients. In each case the white blood cell count returned to normal before the program was completed.

The side effects observed were those to be expected with the use of intralesional administration of interferon. It was noted that the side effects were more frequent at the first injection and became fewer as the program progressed.

CLINICAL STUDY II

PATIENTS AND METHODS

Patients

One hundred sixty five patients, 29 females and 136 males, each with biopsy proven primary basal cell carcinoma (BCC) of nodular (89 patients) or superficial (76 patients) types were included in the study which was a randomized, double-blind, parallel group, multicenter study design. The lesions, which varied in size from 15 mm$^2$ to 400 mm$^2$ were located on the back (45), neck (20), shoulder (24), forehead (11), head and face (27), trunk (17) and extremities (21).

Each patient was in good health and elected to be treated with interferon alpha-2b rather than undergo other ablative or surgical procedures.

Laboratory Test and Treatment

The laboratory tests and treatment were the same as described for Clinical Study I except evaluations of the patients after completion of the treatment were continued at one, four, eight and twelve weeks after treatment.

Response Criteria

Punch biopsy was performed for histopathologic evaluation of the test site.

The following Tables show the results of treatment of basal cell carcinoma with purified recombinant DNA human interferon alpha-2b in Clinical Study II.

TABLE III

Results of Treating Basal Cell Carcinoma with Interferon Alpha-2b (16-week biopsy).

| Treatment | N# | Punch Biopsy Results* Negative | Punch Biopsy Results* Positive | Percent of Lesions Cured |
|---|---|---|---|---|
| Interferon | 120 | 102 | 18 | 85 |
| Placebo | 42 | 12 | 30 | 29 |
| TOTAL | 162 |   |   |   |

*Biopsy results: Negative = tumor absent, Positive = tumor present.
Biopsy data are missing for three Interferon-treated patients.

As is apparent from the data in Table III, 85% of the treated basal cell carcinomas were eliminated, whereas only 29% of the placebo treated lesions tested negative in the punch biopsy. The punch biopsy was taken 16 weeks after the treatment began.

TABLE IV

Results of Treating Basal Cell Carcinoma with Interferon Alpha 2b, by Lesion Type (16-week Biopsy)

| Type of BCC | Treatment | N | Punch Biopsy Results* Negative | Positive | % Cured |
|---|---|---|---|---|---|
| Super-ficial | Interferon | 56 | 49 | 7 | 88 |
|  | Placebo | 19 | 6 | 13 | 32 |
| Nodular | Interferon | 64 | 53 | 11 | 83 |
|  | Placebo | 23 | 6 | 17 | 26 |

*Biopsy results: Negative = tumor absent, Positive = tumor present.
Biopsy data are missing for three Interferon-treated patients.

The results in Table IV demonstrate that efficacy of interferon alpha-2b is independent of lesion type.

TABLE V

Results of Treating Basal Cell Carcinoma with Interferon Alpha-2b, by Lesion Size (16-week biopsy)

| Baseline Test Lesion Area (sq mm) | N | Punch Biopsy Results (Week 16)* Negative | Positive | % Cured |
|---|---|---|---|---|
| <50 | 53 | 42 | 11 | 79 |
| >50–100 | 35 | 33 | 2 | 94 |
| >100–200 | 24 | 20 | 4 | 83 |
| >200 | 8 | 7 | 1 | 88 |
| TOTAL | 120 | | | |

*Biopsy results: Negative = tumor absent, Positive = tumor present.
Biopsy data are missing for three patients.

The results in Table V show that the lesion size did not significantly affect the efficacy of the interferon.

It was found during the treatment period, the mean area of the test sites treated with interferon alpha-2b increased progressively, and by the 4-week visit (first week post treatment), had increased 64% above the area measured at baseline (pretreatment lesion size); this was in contrast to an insignificant change in area of placebo-treated lesions. At the 8-week visit, mean lesion area in the interferon treated lesions had decreased by 26% from baseline compared to a decrease of 11% in the placebo treatment group. The area of the interferon lesions progressively decreased and at the 16-week evaluation, the mean decrease in lesion area was 46% whereas the mean decrease in lesion area at the 16 week evaluation in the placebo treatment group was 16%, significantly less than the interferon treated group. The patients were followed for one year and the results indicated that the overall cure rate at the end of the year was 81%.

Side Effects

No life threatening or serious side effects were found. The side effects reported were almost always mild or moderate in severity and were similar to those reported in Clinical Study I.

The following are a description of a clinical study on the treatment of large basal cell carcinomas by intralesional administration of purified human recombinant DNA interferon alpha-2b.

CLINICAL STUDY III

PATIENTS AND METHODS

Ten patients, all males, each with biopsy proven basal cell carcinoma lesions of nodular (5 patients) and superficial (5 patients) types were included in the study which was an open-label study. The mean lesion area at baseline (pretreatment measurement) was 6.1 cm² and ranged from 3.4 to 9.9 cm².

The test lesions were located on the back (4 patients), shoulder (2 patients), neck (2 patients), arm (1 patient) and temple (1 patient).

Each patient was in good health and elected to be treated with interferon alpha-2b rather than undergo other ablative or surgical procedures.

Laboratory Test

Laboratory tests were performed at baseline during treatment and during follow-up.

Treatment

Treatments were conducted with freeze-dried purified human recombinant DNA interferon alpha-2b which was in vials containing $5 \times 10^6$ I.U. Each lesion of from about three to ten cm² in area was injected intralesionally with about $0.5 \times 10^6$ I.U./cm² of original lesion area. The procedure was repeated for a total of three injections per week for three weeks resulting in a total dosage in this procedure of 16 to $45 \times 10^6$ I.U. per patient, depending on the lesion size.

Patients were evaluated during the treatment for clinical response and side effects. Evaluations were made during the three week treatment period and for 13 weeks after the completion of treatment. Systemic side effects (i.e. flu-like symptoms were treated and controlled with oral acetaminophen.

The following Table VI show the results at the end of 16 weeks.

TABLE VI

Results from End-of-Study (16 week) Biopsies (3 punch biopsies)

| Patient | Type of Lesion | Baseline Area (cm²) | Results[3] Presence or Absence of Tumor |
|---|---|---|---|
| 2 | superficial | 6.5 | absent |
| 4 | superficial | 5.3 | absent |
| 5[1] | superficial | 8.5 | present[2] |
| 6 | superficial | 9.5 | absent |
| 10 | superficial | 6.5 | absent |
| 1 | nodular | 3.4 | absent |
| 3 | nodular | 4.5 | absent |
| 7 | nodular | 3.5 | absent |
| 8 | nodular | 3.8 | absent |
| 9 | nodular | 9.9 | present |

[1]Lesion had nodular component.
[2]Two biopsies were negative (tumor absent), the third was positive (tumor present).
[3]Results of three biopsies per patient.

The results in Table VI show that treatment with interferon alpha-2b resulted in no tumors remaining in 80% of the patients.

The following Table VII shows the changes in lesion sizes as a result of treatment with interferon alpha-2b.

TABLE VII

Effect of Interferon Alpha 2-b on Lesion Size

| Lesion Type Patient | Lesion Area (cm²) | | |
|---|---|---|---|
|  | Baseline | Posttreatment | Percent Change |
| Superficial |  |  |  |
| 2 | 6.5 | 3.4 | −48 |
| 4 | 5.3 | 3.5 | −34 |
| 5 ¶ | 8.5 | 8.6 | +1 |
| 6 | 9.5 | 0.1 | −99 |
| 10 | 6.5 | 2.0 | −69 |
| Nodular |  |  |  |
| 1 | 3.4 | 2.0 | −41 |

TABLE VII-continued

| Lesion Type | Effect of Interferon Alpha 2-b on Lesion Size | | |
|---|---|---|---|
| | Lesion Area (cm$^2$) | | |
| Patient | Baseline | Posttreatment | Percent Change |
| 3 | 4.5 | 3.7 | −18 |
| 7 | 3.5 | 0.3 | −91 |
| 8 | 3.8 | 1.8 | −53 |
| 9 ¶ | 9.9 | 10.0 | +1 |
| MEAN | 6.1 | 3.4 | −45 |

Week 16 evaluation.
¶ Tumor present at end of study.

The data in Table VII show that all lesions had changes in lesion area. For those lesions that had negative biopsies at week 16, the measured area of the lesional site had decreased from 18% to 99%. In these biopsy negative lesions, the measurable area at Week 16 could be characterized as pigmentary and textural skin changes. At the last visit prior to biopsy, the lesion sites that were tumor free were variously described as slightly depressed or hypopigmented patches, pink in color, or mildly erythematous. Of the patients cured, six listed cosmetic results as excellent and two as very good.

The two patients (No. 5 and 9) with tumor present at Week 16 had slight increases in lesion area. For these patients, the lesions were described as a pearly pink nodule or nodular lesion. These descriptions indicate that the presence of tumor could be determined by clinical examination.

Side Effects

No life threatening or serious side effects were found. Those present were predominantly the expected flu-like symptoms which accompany treatment with interferon. These symptoms were most often reported during the first week of treatment, with fewer reports during weeks 2 and 3. Three patients reported mild local reactions such as pain, burning or itching.

Analyses indicated no detectable levels of circulating interferon neutralizing factors in any patient.

The results of the above described clinical testing programs show that intralesional injection of purified recombinant DNA human interferon alpha-2b is a safe, effective treatment for basal cell carcinoma.

What is claimed is:

1. A method for treating human basal cell carcinoma comprising intralesionally administering to a human in need of such-treatment a sufficient amount of purified recombinant DNA human interferon alpha-2b to be effective as an anti-basal cell carcinoma agent.

2. A method of claim 1 wherein $13.5 \times 10^6$ I.U. of said interferon is administered during a three week period.

3. A method of claim 1 from $13.5 \times 10^6$ to $45 \times 10^6$ I.U. of said interferon is administered during a three week period.

4. A method of claim 1 wherein $16 \times 10^6$ I.U. of said interferon is administered during a three week period.

* * * * *